US009066864B2

(12) United States Patent
Niedermann et al.

(10) Patent No.: US 9,066,864 B2
(45) Date of Patent: Jun. 30, 2015

(54) USE OF LIQUID MEDIUM EXCHANGE BY CROSS FLOW FILTRATION IN THE PREPARATION OF DRUG SUSPENSIONS

(75) Inventors: Hans Peter Niedermann, Bubenheim (DE); Heiko Bothe, Saulheim (DE)

(73) Assignee: Intervet Inc., Summit, NJ (US)

( * ) Notice: Subject to any disclaimer, the term of this patent is extended or adjusted under 35 U.S.C. 154(b) by 57 days.

(21) Appl. No.: 13/979,231

(22) PCT Filed: Jan. 11, 2012

(86) PCT No.: PCT/EP2012/050336
§ 371 (c)(1),
(2), (4) Date: Jul. 11, 2013

(87) PCT Pub. No.: WO2012/095439
PCT Pub. Date: Jul. 19, 2012

(65) Prior Publication Data
US 2013/0281425 A1 Oct. 24, 2013

Related U.S. Application Data

(60) Provisional application No. 61/431,942, filed on Jan. 12, 2011.

(51) Int. Cl.
A61K 9/10 (2006.01)
A61K 31/546 (2006.01)
A61K 47/06 (2006.01)
A61K 47/14 (2006.01)

(52) U.S. Cl.
CPC ............... *A61K 9/10* (2013.01); *A61K 31/546* (2013.01); *A61K 47/06* (2013.01); *A61K 47/14* (2013.01)

(58) Field of Classification Search
None
See application file for complete search history.

(56) References Cited

FOREIGN PATENT DOCUMENTS

| CN | 1735403 A | 2/2006 | | |
|---|---|---|---|---|
| EP | 1 175 499 B1 | 3/2005 | | |
| WO | 01/21290 A1 | 3/2001 | | |
| WO | 03/063877 A1 | 8/2003 | | |
| WO | 2004/037265 A1 | 5/2004 | | |
| WO | WO2004/037265 | * | 5/2004 | ........... A61K 31/546 |
| WO | 2004054545 A1 | 7/2004 | | |

OTHER PUBLICATIONS

Dalwadi et al., "Comparison of Diafiltration and Tangential Flow Filtration for Purification of Nanoparticle Suspensions", Pharmaceutical Research, 2005, pp. 2152-2162, vol. 22(12).
Holdich et al., "Crossflow Microfiltration for Mineral Suspension Thickening and Washing", Minerals Engineering, 1996, pp. 243-257, vol. 9(2).
Lohr et al., "A survey on the use of Cobactan suspension 2.5% in animals (cattle)—results relevant to veterinary practice", Tierarztl. Umschau, 2004, pp. 352-355, vol. 59 (Translation Attached).

(Continued)

*Primary Examiner* — Trevor Love

(57) ABSTRACT

Disclosed is a method of making particles of a drug wherein use is made of diafiltration. The diafiltration can be with anti-solvent, in which case a precipitate is obtained of particles as such. The diafiltration can also be with a pharmaceutically acceptable suspension medium. In that case several process steps of isolating, drying, transporting of particles can be avoided, because the suspension resulting from the synthesis of the particles is directly turned into a final drug product formulation.

10 Claims, 2 Drawing Sheets

| 1 | filtration unit |
|---|---|
| 2 | membrane |
| 3 | inlet flow (a) |
| 4 | outlet flow (b) |
| 5 | outlet flow (c) |
| 6 | mixing unit |
| 7 | vessel |
| 8 | agitator |
| 9 | inlet antisolvent (d) |
| 10 | inlet permeate c |
| 11 | outlet flow (a) |
| 12 | pump unit |
| 13 | outlet flow (a) to separation unit |
| a-d | diverse liquid flows |

(56) References Cited

OTHER PUBLICATIONS

Sheth et al., "Nanofiltration-based diafiltration process for solvent exchange in pharmaceutical manufacturing", Journal of Membrane Science, 2003, pp. 251-261, vol. 211.

European Search Report for EP Application No. 11 15 0745, dated Jun. 10, 2011.
International Search Report for corresponding PCT/EP2012/050336, mailed on Jun. 22, 2012.

* cited by examiner

| | |
|---|---|
| 1 | filtration unit |
| 2 | membrane |
| 3 | inlet flow (a) |
| 4 | outlet flow (b) |
| 5 | outlet flow (c) |
| 6 | mixing unit |
| 7 | vessel |
| 8 | agitator |
| 9 | inlet antisolvent (d) |
| 10 | inlet permeate c |
| 11 | outlet flow (a) |
| 12 | pump unit |
| 13 | outlet flow (a) to separation unit |
| a-d | diverse liquid flows |

| | |
|---|---|
| 1 | filtration unit |
| 2 | membrane |
| 3 | inlet flow (a) |
| 4 | outlet flow (b) |
| 5 | outlet flow (c) |
| 6 | mixing unit |
| 7 | vessel |
| 8 | agitator |
| 9 | inlet antisolvent (d) |
| 10 | inlet permeate c |
| 11 | outlet flow (a) |
| 12 | pump unit |
| 13 | outlet flow (a) to filling line |
| a-d | diverse liquid flows |

USE OF LIQUID MEDIUM EXCHANGE BY CROSS FLOW FILTRATION IN THE PREPARATION OF DRUG SUSPENSIONS

CROSS-REFERENCE TO RELATED APPLICATIONS

This application is a national stage entry under 35 U.S.C. §371 of PCT/EP2012/050336, filed on Jan. 11, 2012, which claims priority to U.S. Provisional Application No. 61/431, 942, filed on Jan. 12, 2011. The content of PCT/EP2012/050336 is hereby incorporated by reference in its entirety.

FIELD OF THE INVENTION

The invention pertains to the preparation of pharmaceutical suspensions.

BACKGROUND OF THE INVENTION

Cross-flow filtration (also referred to as diafiltration) technology has been used widely in industry globally and is largely applied to process aqueous feed streams. When purifying water, it can be very cost effective in comparison to the traditional evaporation methods. The a-thermal solvent exchange in solutions from one organic synthesis step to the next step in pharmaceutical manufacturing by diafiltration using organic solvent resistant membranes has been suggested (Sheth J. P., et al, Journal of Membrane Science 211 (2003), 251-261.

However the use of cross flow filtration technology for liquid medium exchange between pharmaceutical suspensions in the working-up of the drug from its synthesis so as to obtain the drug in particulate form, or in the direct production of a drug product comprising the drug, wherein the step of first isolating particles can be bypassed has been not described before.

In pharmaceutical suspensions it is generally desired to provide the drug in the form of particles, particularly crystalline particles, of a relatively small size, and of a desired size distribution. The drug particles are ultimately formulated into a drug product, in the form of a suspension of said particles.

The formation of the desired particle sizes and the desire of obtaining a stable suspension in a pharmaceutically acceptable liquid medium, presents several technical challenges. One is that obtaining particles, notably crystalline particles, requires precipitation from a solution or suspension in a controlled way. To this end, e.g. in the case of cefquinome sulfate, acetone is added to water, or to a mixture of water and acetone, so as to force precipitation. This brings about a relatively high volume of solvent (or, rather, the anti-solvent acetone), which moves the production of commercially viable batch sizes in an uneconomical direction.

It would therefore be desired to provide a method by which particles, notably crystalline particles, of the desired particle size can be obtained on the basis of a substantially reduced volume of anti-solvent.

It would also be desired to provide a method by which the particles agglomerates to bigger particle collective to ease the filtration step if the particles should be separated as such.

Further, in the existing processes, the final drug product is a suspension, in a pharmaceutically acceptable liquid medium such as ethyl oleate, of the crystalline particles as produced in the desired particle size at an earlier stage of the process. The overall process therefore requires not only the controlled precipitation of the particles, but also isolation, drying, packaging, transportation, and formulation. It would be desired to be able to dispense with one or more of the steps in between the formation of the particles (viz. in a suspension) and the production of the final formulation (also a suspension).

SUMMARY OF THE INVENTION

In order to better address one or more of the foregoing desires, the invention, in one aspect, presents a method of making a composition comprising particles of a drug, wherein the drug is initially produced in the form of a suspension in a first liquid medium, wherein the suspension is subjected to cross-flow filtration against a further liquid medium, said further liquid medium being selected from media behaving as an anti-solvent for the drug and pharmaceutically acceptable media capable of retaining the drug as a suspension.

In another aspect, the invention provides the use of a diafiltration method in the production of particles, particularly crystalline particles of a drug just as agglomerates of such particles to ease the filtration step.

In yet another aspect, the invention provides a method of isolating drug particles from a solution or suspension in a liquid medium by the addition of an anti-solvent for the drug, wherein anti-solvent is added by means of diafiltration.

In a further aspect, the invention provides a method of making a pharmaceutical formulation comprising a suspension of a drug in a pharmaceutically acceptable liquid medium, wherein the formulation is made from a crystalline suspension in a processing liquid medium, and wherein said pharmaceutically acceptable liquid medium is substituted for said processing liquid medium by means of diafiltration.

In a still further aspect, the invention pertains to the use of liquid medium exchange by diafiltration, in the preparation of suspensions of drugs.

DETAILED DESCRIPTION OF THE INVENTION

Figure 1:
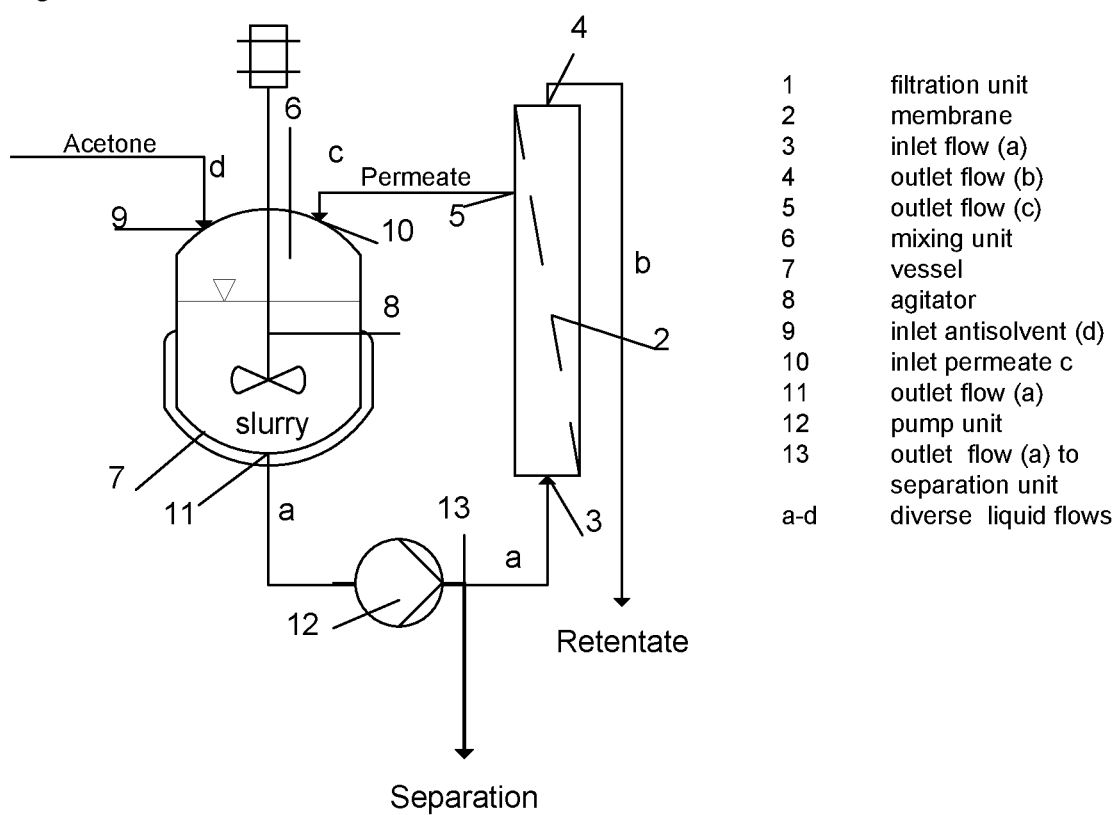
FIG. 1 shows a schematic set-up of an embodiment of the invention in which diafiltration is used in the generation of drug particles.

In a broad sense, the invention is based on the judicious recognition to use diafiltration as a method for exchange of liquid media, in the preparation of suspensions of drugs. According to the invention, the method can be applied either in the working-up of the drug from its synthesis so as to obtain the drug in particulate form, or in the direct production of a drug product comprising the drug, wherein the step of first isolating particles can be bypassed. Pharmaceutical suspensions are uniform dispersions of solid drug particles in a liquid medium in which the drug is practically insoluble.

Examples of Pharmaceutical Suspensions are e.g. antibacterial injectable suspensions for intramuscular and subcutaneous administration, antibacterial suspensions for intramammary administration, antacid oral suspensions, antibacterial oral suspensions, analgesic oral suspensions, anthelmintic oral and subcutaneous injectable suspensions, anticonvulsant oral suspensions, antifungal oral suspensions.

The term "practically insoluble" as used herein applies to drugs that are essentially totally insoluble in the suspending medium or are at least poorly-soluble in such medium (solubility less than about 10%).

In one embodiment the pharmaceutical suspension is a non-aqueous suspension i.e. the liquid medium is non-aqueous, e.g. oily.

Any practically insoluble drug may be beneficially used in the pharmaceutical composition of the present invention. In this respect, it should be appreciated that while the specification will here list various drugs that are typically considered to be practically insoluble, many drugs (whether considered practically insoluble or not) will have versions (crystalline forms, polymorphs, etc) that are in fact practically insoluble. Also, it is to be appreciated that drugs developed in the future that are also considered to be practically insoluble, are also to be included within the scope of the present invention.

While the specific benefits of the method of the present invention have been established by the inventors for cephalosporin antibiotics, such as cefquinome and cefalonium, similar benefits will be available for other classes of drugs such as other antibiotics, anthelmintics, anti-hypertensives, immunosuppressants, anti-inflammatories, analgesics, diuretics, antiepileptics, cholesterol lowering drugs, hormons hypoglycemics, antiviral drugs, nasal decongestants, anti-arrthrytics, anti-cancer drugs, anti-parasitics, proteins, peptides, CNS stimulants, CNS depressants, 5 HT inhibitors, anti-schizophrenics, anti-Alzheimer drugs, anti-psoriatics, steroidals, oligonucleotides, anti-ulcer drugs, proton pump inhibitors, anti-asthmatics, thrombolytics and vitamins.

Even though the following description will mainly describe embodiments of the invention with respect to cephalosporin antibiotic drugs, it is to be appreciated that the invention is not to be so limited. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Whilst the step of particle generation will result in a suspension (particularly a sterile suspension), the liquid medium of the suspension will have to be changed in favor of an anti-solvent in order to have the particles precipitate (e.g. acetone in the case of cefquinome sulfate). Normally, it would be realized by a solvent exchange using thermal unit operations like distillation or evaporation. This would be easy to handle if the anti solvent boils at a higher temperature as the liquid medium. Troubles would occur if the product is temperature sensitive or if the anti solvent boils at a lower temperature as the liquid medium. One solution is to add a high amount of anti-solvent to the liquid medium to force the crystal precipitation. This step, and the relatively high amounts of anti-solvent needed, considerably reduces the batch size at which the drug particles can be produced. The present inventors have found a way of adding the anti-solvent by means of diafiltration (cross-flow filtration). An advantage hereof is that a much lower amount of anti-solvent is required, and the particles can be produced at desired commercial batch sizes.

Thus, in one embodiment, the invention is a method of making a composition comprising particles of a drug, wherein the drug is initially produced in the form of a suspension in a first liquid medium, wherein the suspension is subjected to cross-flow filtration against a further liquid medium, and wherein said further liquid medium is selected from media behaving as an anti-solvent for the drug.

"Anti-solvent" means a solvent in which the product is insoluble. Anti-solvents are known, and when a drug is given, it is within the ambit of the average skills of the artisan to select suitable anti-solvents. In the case of cefquinome or cefquinome sulfate or other acid addition salt, a suitable anti-solvent is acetone or a mixture of water and acetone wherein acetone is the major component. Other suitable anti-solvents are within the ambit of the artisan's skills.

In carrying out the diafiltration of the invention, the composition of the further liquid medium can be changed as desired during the process, e.g. by gradually increasing the amount of acetone in the case of using a mixture of water and acetone as an anti-solvent.

In this embodiment, the composition comprising particles of a drug in fact comprises the isolated (precipitated) particles as such. Some suspensions comprise very small particles of drugs that cannot be separated by conventional filtration methods because the fine particles block the filter and cause a prolonged filtration time. These particles have particle sizes typically in the rage of 0.05-50 µm. By the method of the current invention, agglomerates of such fine particles can be formed using suitable anti-solvents. Such agglomerates can then be separated by conventional filtration methods.

Preferably the agglomeration of the fine particles can be after filtration reversed e.g. by simply agitating suspensions of the particles or under the influence of ultrasound.

In a preferred embodiment, the further liquid medium is selected from pharmaceutically acceptable media capable of retaining the drug as a suspension. As a result, in this embodiment, the invention puts to use the aforementioned diafiltration in a different way. Rather than using the technique in the existing process, viz. at the step of isolation of particles, the preferred embodiment uses the diafiltration of the suspension of drug particles to add the eventual liquid medium of the drug product, i.e. the aforementioned pharmaceutically acceptable suspension medium, e.g. the oily liquid.

In this embodiment, the composition comprising particles of a drug is a pharmaceutical composition in the form of a suspension of the drug in a pharmaceutically acceptable liquid medium. This leads to considerable advantages, in that all of the process steps associated with isolating drug particles can be dispensed with. Thus, rather than involving the steps of isolation, drying, particle size adjustment (micronization), packaging, transportation, and reformulation as a suspension, this embodiment of the invention allows a direct step from a sterile crystal suspension towards a final drug product suspension.

Suspensions of such drugs are e.g. presented as injection preparation in e.g. in suspended in oils such as e.g. ethyl oleate or in the type of esters of saturated coconut and palm kernel oil-derived caprylic and capric fatty acids and glycerine or propylene glycol, known by the trade name of Miglyol.

In one embodiment the drug is a cephalosporin. Cephalosporins are a class of beta-lactam antibiotics generally being considered derivatives of 7-aminocephalosporanic acid. Many cephalosporins are on the market. The non-proprietary names generally start with "cef" (and sometimes ceph). Preferred cephalosporins include cefclidine, cefepime, cefluprenam, cefoselis, cefozopran, cefpirome, ceftiofur, cephapirin, cefotaxime, cefadroxil, cephalexin, cefovectin, cefazolin, cephalothin, and cefquinome. More preferably the cephalosporin is cefquinome, and most preferably a cefquinome acid addition salt.

In order to prepare an acid addition salt of cefquinome, a suitable acid is added to the betaine solution. These acids can be organic or inorganic, monobasic or dibasic acids, with mineral acids being preferred.

Suitable acids include, e.g., HCl, HBr, HI, HF, $H_2NO_3$, $HClO_4$, HSCN, aliphatic mono-, di- or tricarboxylic acids, for example acetic acid, trifluoro acetic acid, trichloro acetic acid, or a preferred physiologically acceptable acid, such as, for example, the maleic acid, so as to provide a salt having the monomaleate anion $HOOCCH\!=\!CHCOO^-$. Another suitable organic acid is naphthoic acid. Preferred cefquinome acid addition salts include cefquinome dihydrochloride, cefquinome dihydroiodide, cefquinome sulfate, cefquinome-6-hydroxy naphthoate, cefquinome-naphthoate, cefquinome 2,4 dihydroxy benzoate.

The most preferred salt is the cefquinome sulfate.

Cephalosporins generally come as suspensions in a pharmaceutically acceptable liquid medium, particularly in the form of a suspension in an oily base, being a vegetable oil or a mineral oil or mixtures thereof, e.g. peanut oil, castor oil, ethyl oleate, liquid paraffin, MCT oil (see below) or, Miglyol® (see below). The base preferably comprises a pharmaceutical acceptable low viscosity oily medium, such as medium chain triglyceride or a mixture of medium chain triglycerides. Medium chain triglycerides (MCT oil) have fatty acid chains of 6-12 carbon atoms and for the medically refined grades of MCT oil each chain has 8-10 carbon atoms. The MCT oil may comprise either triglycerides of the C8-C10 fatty acids, or propylene glycol diesters of these fatty acids or a mixture of both triglycerides and propylene glycol diesters. Preferably these C8-C10 fatty acids are fully saturated, such as n-caprylic and n-capric acids. These are conveniently prepared by the commercial fractionating of naturally occurring vegetable (e.g. coconut) oil to give mainly C8-10 fatty acids followed by esterification of these acids with a chosen alcohol. Fractionated vegetable oil having the desired composition is commercially available. Proprietary examples of such oils are Miglyol® 812 as capric/caprylic triglycerides and Miglyol® 840 as propylene glycol dicaprylate/caprate. Most preferred is Miglyol® grade 812.

Depending on the pharmaceutically acceptable liquid medium used in the drug product suspension and the liquid medium in which the drug crystal suspension is produced, these liquid media may or may not be sufficiently miscible with each other so as to conduct the diafiltration. "Miscible" means that the liquid media mix in all proportions, forming a homogeneous solution.

In the latter case it is preferred to conduct an additional diafiltration with an intermediate (second) liquid medium, that is miscible with both the first liquid medium (in which the crystals are produced) and the further liquid medium (the pharmaceutically acceptable liquid medium in the drug product). In the table below, guidance is given on several example liquids used. The possible liquids are not limited to the ones mentioned herein, and the person skilled in the art will be able to easily determine whether or not liquids are miscible, so as to decide whether or not the diafiltration can be conducted directly, or via an intermediate liquid.

TABLE

Miscibility of various liquids

| agent 1 (□ [mPas]) | agent 2 (□ [mPas]) | agent 3 (□ [mPas]) | miscible |
|---|---|---|---|
| acetone (0.32) | Miglyol ® (30) | — | yes |
| acetone (0.32) | ethyloleate (6.5) | — | yes |
| acetone (0.32) | liquid paraffin (110-230) | — | no |
| Miglyol ® (30) | liquid paraffin (110-230) | — | yes |
| Miglyol ® (30) | ethyloleate (6.5) | — | yes |
| ethyloleate (6.5) | liquid paraffin (110-230) | — | yes |
| Miglyol ® (30) 32% | acetone (0.32) 40% | liquid paraffin (110-230) 22% | yes |
| Miglyol ® (30) 35% | acetone (0.32) 50% | liquid paraffin (110-230) 15% | yes |
| ethyloleate (6.5) 25% | acetone (0.32) 25% | liquid paraffin (110-230) 50% | yes |
| ethyloleate (6.5) 22% | acetone (0.32) 30% | liquid paraffin (110-230) 48% | yes |

In the invention, a drug suspension is subjected to cross-flow filtration against a further liquid medium, said further liquid medium being selected from media behaving as an anti-solvent for the drug and pharmaceutically acceptable media capable of retaining the drug as a suspension. It will be understood that the pharmaceutically acceptable liquid medium will generally not be a solvent for the drug, as it retains a suspension thereof. It will also be understood, in view of the above embodiment to make use of an intermediate liquid medium, that the invention encompasses the indirect exchange of the liquid medium in the initially obtained suspension with the final pharmaceutically acceptable liquid medium.

Cross-flow filtration (also referred to as diafiltration) is a known technique, normally used for entirely different purposes. Typical uses include waste-water treatment, the production of purified water or salt water purification. A typical use in pharmaceutical industry is for the enrichment of a fermentation slurry. A further typical use in health care environment is the well known dialysis of human blood.

As termed in the "Dictionary of Filtration and Separation," diafiltration is a membrane based separation that is used to reduce, remove or exchange salts and other small molecule contaminant from a process liquid or dispersion. The process essentially involves passing a feed flow across a membrane filter on one side, and passing a clean liquid across the membrane filter on the other side, in the opposite direction. This type of filtration is typically selected for feeds containing a high proportion of small particle size solids (where the permeate is of most value) because solid material can quickly block (blind) the filter surface with dead-end filtration. In batch diafiltration, the process fluid is typically diluted by a factor of two using "clean" liquid, brought back to the original concentration by filtration, and the whole process repeated several times to achieve the required concentration contaminant. In continuous diafiltration the "clean" liquid is added at the same rate as the permeate flow.

Cross-flow filtration refers to the fact that the majority of the feed flow travels tangentially across the surface of a filter, rather than into the filter. The principle advantage of this is that the filter cake (which can blind the filter) is substantially washed away during the filtration process, increasing the length of time that a filter unit can be operational. It can be a continuous process, unlike batch-wise dead-end filtration.

The manner in which the present invention puts to use the technique of diafiltration deviates from the regular uses thereof in several respects. In one respect, the technique is used in the invention to precipitate solids (viz. drug particles), which in classical filtration would mean keeping them as a retentate. In another respect, the technique is used to transfer drug particles from one suspension to another, which is entirely incomparable with normal (filtration-type) used of diafiltration.

In the diafiltration process of the invention, the filter will preferably be a ceramic membrane. Such filters are known, and are made of, e.g., silicon, silicon nitride, silicon oxynitride, silicon carbide, silicides, alumina, zirconium oxide, magnesium oxide, chromium oxide, titanium oxide, titanium oxynitride, titanium nitride, yttrium barium copper oxides, or as composite membrane, made of polymer membranes based on polyvinylalcohols, polyimides, polyacrylamides, polysiloxanes, polydimethylsiloxanes, ethylene-propylene diene, polynorbonene, polyoctenamer, polyurethane, butadiene, nitrile butadiene rubber, polyethylene, polypropylene, polyvinylidene difluoride, derivatives and mixtures thereof, on an inorganic (e.g. ceramic or zeolithe) surface layer The filter membranes can have a variety of shapes, e.g. disk-type or hollow tube-type. It will be understood that the membrane has pores, which presents the skilled person with the choice of a pore size. The lower limit in the present invention is 1 nm diameter. The upper limit is 10 µm.

The diafiltration process can be conducted in equipment known in the art. Typically, the equipment will comprise a filtration unit (1) comprising a tubular or disc diafiltration membrane (2), an inlet (3) for the flow (a) of liquid to be subjected to diafiltration, an outlet (4) for a flow of retentate (b) and an outlet (5) for a flow of permeate (c); said filtration unit comprises fluid connections (flows a and c above) with a mixing unit (6), comprising a vessel (7) provided with an agitator (8), an inlet (9) for a flow of anti-solvent (d), in the figure indicated with reference to acetone, an inlet (10) for the flow of permeate (c), and an outlet (11) for a flow of liquid (a), i.e. a suspension. from the vessel (7) to the filtration unit (1), driven by a pump unit (12).

In FIG. 1 the equipment is presented for use in generating cefquinome (or other drug) crystalline particles, with reference to the use of acetone as the anti-solvent flow (d) and comprising a valve (13) allowing the flow of liquid (a) to either be led to a separation unit (not shown) so as to obtain solid particles, or to the filtration unit (1) for further diafiltration.

Figure 2:
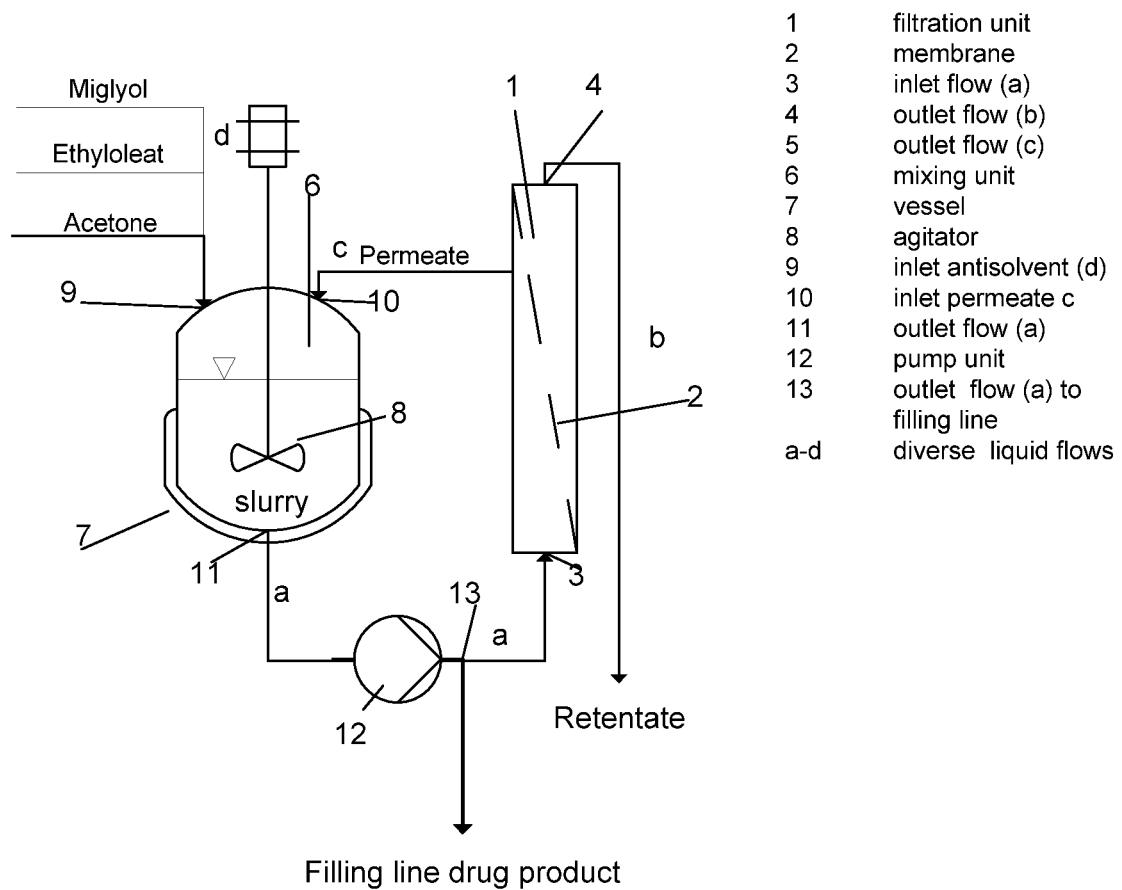
FIG. 2 shows a schematic set-up of an embodiment of the invention in which diafiltration is used in directly converting a sterile drug suspension as obtained in a particle generation step, into a drug product (suspension formulation in a pharmaceutically acceptable liquid medium).

In FIG. 2 the aforementioned equipment is presented for use in generating a cefquinome (or other drug) drug product (suspension), with reference to the use of a choice of carrier liquids as the anti-solvent flow (d) and wherein the valve (13) allows the flow of liquid (a) to either be led to a drug product filling line (not shown), or to the filtration unit (1) for further diafiltration.

The judicious choice of this method leads to advantages that are particularly enjoyed when making suspensions as drug products. Therefore the invention, in one aspect, also relates to the use of a diafiltration method in the production of particles of a drug.

The reason that the method provides such advantages is, inter alia, that the production of suspensions as drug products requires a step of adjusting particle size, and requires a step of formulating the drug product as a suspension in a pharmaceutically acceptable liquid. The former step generally requires the use of liquids, such as acetone, that are not pharmaceutically acceptable. The use of a diafiltration method according to the invention, presents a much more economical process, with a lower risk of losing sterility in intermediate process steps, than in classical processes where drug particles first need to be isolated, and later reformulated.

In this respect, in a further embodiment, the invention also pertains to the use of liquid medium exchange by diafiltration, in the preparation of suspensions of drugs. In another aspect, the invention relates to a method of making a pharmaceutical formulation comprising a suspension of a drug in a pharmaceutically acceptable liquid medium, wherein the formulation is made from a crystalline suspension in a processing liquid medium, and wherein said pharmaceutically acceptable liquid medium is substituted for said processing liquid medium by means of diafiltration.

In yet another embodiment, the invention also pertains to a method of isolating drug particles from a solution or suspension in a liquid medium (particularly a sterile suspension), by the addition of an anti-solvent for the drug, wherein anti-solvent is added by means of diafiltration. The judicious insight to transport existing diafiltration technology to the entirely different field of the preparation of particles of a drug brings about specific advantages. Particularly, since the anti-solvent generally is not a pharmaceutically acceptable liquid, it is desired to use as low an amount thereof as possible.

Moreover, in the case of drugs for parenteral administration the production of a suspension of particles, notably of crystalline drug, it is important that sterility be maintained. This means that also the anti-solvent needs to be sterile, and needs to be used in a sterile equipment area. This adds to the technical complexity, and costs, when relatively high amounts of anti-solvent need to be used.

In summary, the invention presents a method of making particles of a drug, wherein use is made of diafiltration. The diafiltration can be with anti-solvent, in which case a precipitate is obtained of particles as such. The diafiltration can also be with a pharmaceutically acceptable suspension medium. In that case several process steps of isolating, drying, transporting of particles can be avoided, because the suspension resulting from the synthesis of the particles is directly turned into a final drug product formulation.

The invention is further illustrated with reference to the following, non-limiting examples, and the accompanying drawings.

EXAMPLES

General Set Up of the Experiments

The diafiltration trials were done based on a cefquinome sulfate suspension with contents of 7.5-8% cefquinome sulfate in a mixture of acetone and water with a ratio of 2:1. as described in PCT/EP2010/060376.

The suspension was given to a jacketed and stirrable reservoir. By switch on the pump the loop was started. The desired temperature could be controlled by cooling the jacketed vessel. According to the valve position, the permeate was recirculated into the reservoir or discharged during the concentration step and diafiltration step.

The suspension was concentrated to the desired value (normally to two third or the half of the initial concentration). Afterwards acetone was added with the same rate as the permeate left the loop, so the volume kept constant. The amount of the added acetone determined the diafiltration factor D (normally D=2.2) and finally the residual water content in the final suspension. After the diafiltration was finished, the suspension was filtered and dried.

In cases of change of suspending agents (anti-solvents) the acetonic suspensions were diafiltrated with the appropriate agent (anti-solvent) producing the corresponding stem suspensions.

Example 1

The study was done on a ceramic membrane with a porosity of 150 kD. 0.7 L of a crystal suspension was concentrated to 0.35 L and then diafiltrated with 0.8 L pure acetone at a steady volume. During this process step the water content decreases to 7.5%. The success of the diafiltration was tested with filterability tests on a pressure filter. Therefore a part of the original suspension was diluted with acetone to an acetone:water ratio of 29:1 v:v and filtered. This filtrate was turbid, a filtration time of 1.4 min/g solid was observed. The diafiltrated suspension was also filtered, a clear filtrate and a filtration time of 0.6 min/g solid was observed.

Analytical Results water content of final filtrate: 7.5% (by density measurement)
specific filtration time to separate the crystals after diafiltration: 0.6 min/g
specific filtration time to separate the crystals after dilution to 29:1 v:v acetone/water: 1.4 min/g

Example 2

Example 2 was performed according to Example 1 with a diafiltration factor D=1.5, resulting in a water content of 10% for the final suspension and a filtration rate of 1.3 min/g.

Example 3

Example 3 was performed according to Example 1 with a diafiltration factor D=2.2, resulting in a water content of 5% for the final suspension and a filtration rate of 0.2 min/g.

Example 4

Example 4 was performed according to Example 1 with a diafiltration factor D=3.0, resulting in a water content of 2% for the final suspension and a filtration rate of 0.1 min/g.

Example 5

Scale Up

Example 5 was performed according to Example 1 with a volume of 5 L, using a membrane with a surface of 0.2 m$^2$, ten times larger as for lab scale, and with a diafiltration factor D=2.5, resulting in a water content of 2% for the final suspension and a filtration rate of 0.1 min/g. The time needed for concentration and diafiltration was half the time as for the appropriate experiments, due to doubling the specific surface area per suspension volume. No scale up effect was detected.

Example 6

Example 6 was performed according to Example 5 with a diafiltration factor D=2.5, resulting in a water content of 2.3% for the final suspension and a filtration rate of 0.1 min/g, but using a 50 kD ceramic membrane

Example 7

Example 7 was performed according to example 1, using ceramic discs with a porosity of 60 nm and an appropriate equipment. 6.1 L of the crystal suspension was diafiltrated with 25 L of acetone, resulting in a calc. water content of lower than 1%. The final suspension was filtrated with a filtration rate of <0.1 min/g.

Example 8

Cefalonium-dihydrat was suspended in acetone:water 2:1, resulting in a suspension of 10% cefalonium-dihydrat related to water. The diafiltration process was carried out with the same filter equipment as described in example 7.

4.7 L of the suspension was diafiltrated with 23 L of acetone, resulting in a water content <1%. The final suspension was concentrated to a volume of 4 L and filtrated with a filtration rate of <0.1 min/g.

Solvent Change to Formulation Suspensions

Example 9

The initial suspension for this experiment had a content of 7.5-8% Cefquinome sulfate in a mixture of acetone and water with a ratio of 2:1.

The trial was performed by
1. concentrating at 20° C. of the initial suspension with X=1.6,
2. by diafiltration at 20° C. with acetone with D=2.5 (residual water content less than 3%),
3. diafiltration with ethyloleate at 30° C. with D=5.3 (residual acetone content less than 1%)
Membrane type: porosity 150 kD; area 220 cm$^2$ The resulting ethyloleate suspension had an acetone content <0.2%, water content <0.4% and a cefquinome sulphate content of 8.6%.

Example 10

Diafiltration with Ethyloleate and Liquid Paraffin as Solutizing Agents

Example 8 was performed according to Example 7 with D=2.0 for diafiltration with ethyloleate at 30° C., followed by diafiltration with liquid paraffin at 30° C. with D=5.0, resulting in a paraffin suspension with a calculated residual acetone content <0.15% and a calculated residual ethyloleate content <1%.

Example 11

Diafiltration with Miglyol® and Liquid Paraffin as Solutizing Agents

Example 9 was performed according to Example 7 with D=5.0 for diafiltration with Miglyol® at 30° C., resulting in a Miglyol® suspension with a calculated acetone content of <1%. The Miglyol® suspension was then diluted with acetone to come to a acetone content of 20% (D=2) and subsequently diafiltrated with liquid paraffin at 30° C. with D=5.0, resulting in a paraffin suspension with a calculated residual acetone content <0.15% and a calculated residual Miglyol® content <1%.

The invention claimed is:

1. A method of making a pharmaceutical composition comprising particles of a drug, wherein the drug is initially produced in the form of a suspension in a first liquid medium, wherein the suspension is subjected to cross-flow filtration against a further liquid medium, said further liquid medium being a pharmaceutically acceptable media capable of retaining the drug as a suspension, wherein the suspension in the first liquid medium is subjected to cross-flow filtration against a second liquid medium so as to obtain a suspension in the second liquid medium, said suspension in the second liquid medium being subjected to crossflow filtration against the pharmaceutically acceptable liquid medium, wherein the first liquid medium is acetone, a mixture of acetone and water or fractionated vegetable oil, wherein the second liquid medium is acetone, a mixture of acetone and water, fractionated vegetable oil or ethyl oleate, wherein the pharmaceutically acceptable media is paraffin or ethyl oleate; and wherein when the first liquid medium is acetone, the second liquid medium is not acetone, when the first liquid medium is acetone and water, the second liquid medium is not acetone and water and when the first liquid medium is fractionated vegetable oil, the second liquid medium is not fractionated vegetable oil, and when the second liquid medium is ethyl oleate, the pharmaceutically acceptable media is not ethyl oleate.

2. The method according to claim 1, wherein the further liquid medium is a pharmaceutically acceptable medium capable of retaining the drug in suspension, and the produced composition comprising particles of a drug is a suspension of the drug in a pharmaceutically acceptable liquid medium.

3. The method according to claim 1, wherein the second liquid medium is selected from the group consisting of ethyl oleate and fractionated vegetable oil, and the further liquid medium is liquid paraffin.

4. The method of claim 1, wherein the drug is a cephalosporin antibiotic.

5. The method according to claim 2, wherein the drug is a cephalosporin antibiotic.

6. The method according to claim 1, wherein the drug is a cephalosporin antibiotic and the first liquid medium is acetone or a mixture of acetone and water and the pharmaceutically acceptable medium is ethyl oleate.

7. The method according to claim 1, wherein the drug is a cephalosporin antibiotic and the first liquid medium is fractionated vegetable oil, the second liquid medium is acetone or a mixture of acetone and water and the pharmaceutically acceptable medium is liquid paraffin.

8. The method of claim 1, wherein the fractionated vegetable oil is capric/caprylic triglycerides or propylene glycol dicaprylate/caprate.

9. The method of claim 3, wherein the fractionated vegetable oil is capric/caprylic triglycerides or propylene glycol dicaprylate/caprate.

10. The method of claim 7, wherein the fractionated vegetable oil is capric/caprylic triglycerides or propylene glycol dicaprylate/caprate.

* * * * *